United States Patent [19]

Herwig et al.

[11] Patent Number: 5,091,093

[45] Date of Patent: Feb. 25, 1992

[54] PROCESS FOR PURIFYING ACRYLONITRILE EFFLUENT

[75] Inventors: Jens Herwig, Cologne; Arnd Stüwe, Leverkusen; Joachim Grub, Dormagen, all of Fed. Rep. of Germany

[73] Assignee: EC Erdolchemie GmbH, Cologne, Fed. Rep. of Germany

[21] Appl. No.: 725,708

[22] Filed: Jul. 3, 1991

[30] Foreign Application Priority Data

Jul. 12, 1990 [DE] Fed. Rep. of Germany ....... 4022222

[51] Int. Cl.$^5$ .............................................. B01D 61/04
[52] U.S. Cl. .................................... 210/639; 210/652
[58] Field of Search ................ 564/127; 558/383, 324; 55/16, 158; 210/641, 652, 639

[56] References Cited

U.S. PATENT DOCUMENTS 4,083,780  4/1978  Call .................................... 210/652
4,235,983 11/1980  Steigelman et al. ................ 55/16 X Primary Examiner—Frank Spear
Attorney, Agent, or Firm—Sprung Horn Kramer & Woods

[57] ABSTRACT

The effluent arising in the production of acrylonitrile can be purified by adjusting it to a pH value from 4 to 9 and then subjecting it to reverse osmosis at a membrane at a temperature from 10° to 50° C. and a differential pressure of 10 to 80 bar. The flow velocity at the membrane is adjusted to a value from 0.5 to 4 m/second. The concentrate is recycled into the acrylonitrile production process.

17 Claims, 2 Drawing Sheets

PROCESS FOR PURIFYING ACRYLONITRILE EFFLUENT

BACKGROUND OF THE INVENTION

Acrylonitrile (ACN) is a large-scale industrial product which is manufactured almost exclusively by ammoxidation of propene in accordance with the following equation:

$$CH_2=CH-CH_3 + NH_3 + \tfrac{3}{2} O_2 \longrightarrow CH_2=CH-CN + 3 H_2O.$$

Theoretically, about one ton of water is also formed per tonne of ACN. Because the selectivity for the desired ACN is not 100%, however, the quantity of water is greater and amounts to about 1.5 tons or more per ton of ACN. This effluent is loaded with undesired by-products, which include nicotinonitrile (molecular weight MW = 104), fumarodinitrile (MW = 78), succinodinitrile (MW = 80), 3-picoline (MW = 93) and 1-H-pyrazole (MW = 68).

Although considerable internal water circulations are required for recovering the acrylonitrile, for example for quenching the hot reactor exit gases and for separating off acrylonitrile on the one hand and, on the other hand, acetonitrile and hydrogen cyanide by extractive distillation, for which purpose effluents can also be used which contain impurities internal to the system. It is necessary in any case, in order to avoid overfilling of these water circulations, to remove the water of reaction, forming in accordance with the above equation, per unit time from the overall process. It is usual in many cases to subject the effluent ultimately arising after passage through the said internal circulations to an effluent distillation, a vapour condensate and a bottom exit stream, more heavily loaded with waste materials, being obtained. An effluent highly loaded with waste materials is taken off at a suitable place in the overall process and fed to the waste incineration, in order to maintain the concentration level of waste materials in the internal circulations at a suitable level. This rate passed to the waste incineration and the vapour condensate together must always correspond to the water of reaction newly forming per unit time.

The vapour condensate contains, inter alia, the by products listed above by name. Further purification by distillation is not possible because of the volatility of these by-products with steam; the vapour condensate must therefore be disposed of in this form. For this purpose, this vapour condensate is, for example, passed into a biological treatment plant. However, the abovementioned organic nitrogen compounds as by-products, which also include ammonia and cyanide, represent a heavy load for a treatment plant even with adapted microorganisms and are not completely degraded.

According to the current ecology concept, it was therefore desirable further to lower the proportion of the said by-products in the effluent, in order to relieve the downstream biological treatment plant and to enable it to operate more effectively. It has been found, surprisingly, that this aim can be achieved in such a way that acrylonitrile effluents, which are taken off as vapour condensate, can be subjected to reverse osmosis at a membrane.

Admittedly, it is known in principle that effluents can be purified by reverse osmosis. In this case, both constituents present in the ion form and neutral organic molecules are retained. For ionic constituents, the retention in the effluent concentrate is in the range from 95 to 99%; however, the retention of ionic constituents plays only a subordinate part in a vapour condensate. For neutral molecules, however, this retention is highly dependent, inter alia, on the molecular weight. A molecular weight of at least 90, and better at least 100, is in general regarded as the lower limit for efficient retention, while organic neutral molecules of lower molecular weight already show significant breakthrough through the membrane.

SUMMARY OF THE INVENTION

Although the molecular weights of most of the abovementioned by-products are below 100, an effective retention in the effluent concentrate is surprisingly possible by means of the reverse osmosis applied according to the invention. This retention is considerable already in a one-stage application of reverse osmosis and rises to 90% and higher in a two-stage procedure.

A process for purifying the effluent arising in the production of acrylonitrile has now been found which is characterised in that the effluent is adjusted to a pH value from 4 to 9, preferably from 5 to 8, and is then subjected to reverse osmosis at a membrane at a temperature from 10° to 50° C., preferably 20° to 40° C., and a differential pressure of 10 to 80 bar, preferably 15 to 60 bar, the flow velocity at the membrane being adjusted to from 0.5 to 4 m/second, preferably 1 to 3 m/second, particularly preferably 1.5 to 2.5 m/second.

DETAILED DESCRIPTION OF THE INVENTION

All membranes suitable for reverse osmosis can be used as the membranes which can be employed according to the invention, without their chemical structure playing a significant part. Thin-film composite membranes are suitable in a preferred way. Such membranes can be used, for example, in the form of flat membrane modules, tubular modules or spirally wound modules, preferably in the form of tubular modules or spirally wound modules. Examples are, for instance, Wafilin WFC as a tubular membrane or Wafilin WFT as a spirally wound module.

The process according to the invention can in principle be carried out in one stage or a plurality of stages. It is self-evident that the purification effect is greater in a multi-stage procedure; however, the costs incurred increase in a multi-stage procedure. Because the purification is in most cases inadequate in an only one-stage procedure, the multi-stage procedure is preferred. It has been found in particular that a two-stage procedure represents a favourable optimum between costs and result.

It has also been found to be advantageous in a multistage procedure to fit the stages which are nearer the start in the direction of flow of the effluent, preferably the first stage, with a tubular module and to fit the stages further along, preferably the second stage in the case of two stages, with a spirally wound module.

Figure 1:
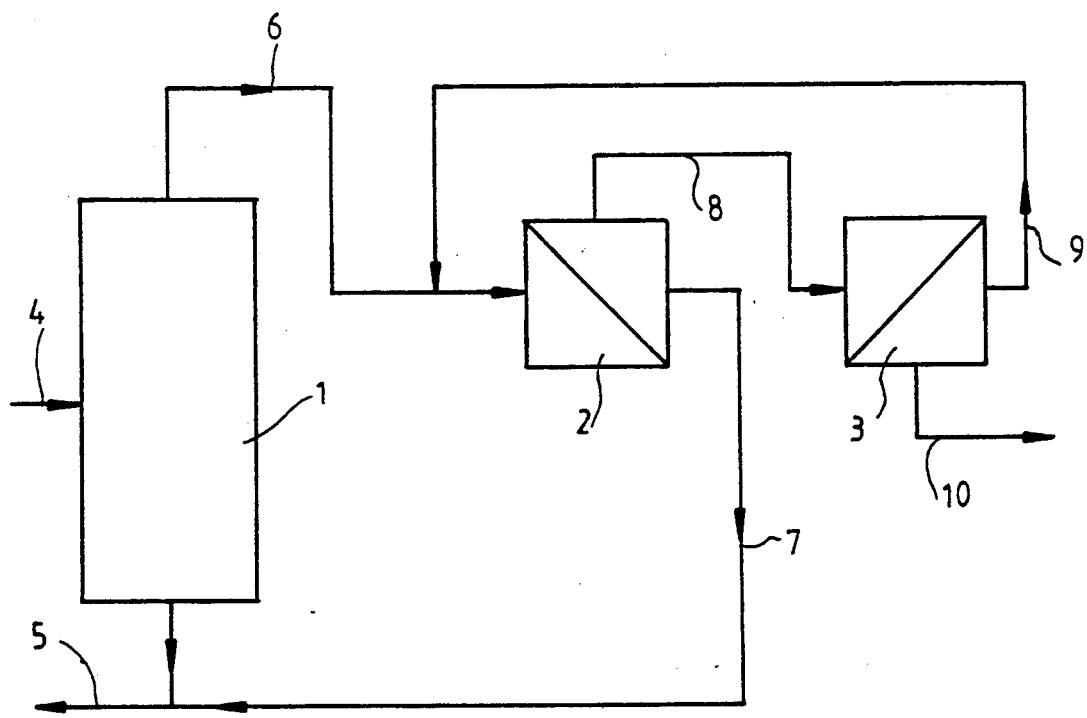
FIG. 1 illustrates the combination of an effluent distillation with a two-stage reverse osmosis treatment of the distillation condensate.

By reference to FIG. 1, the process according to the invention may be illustrated in the preferred two-stage embodiment: the following are shown in FIG. 1 as equipment items: an effluent distillation column (1), a first reverse osmosis stage (2), preferably fitted with a tubular module, and a second reverse osmosis stage (3), preferably fitted with a spirally wound module. The following material streams are shown in FIG. 1: an effluent stream (4) from the ACN plant, a bottom exit stream (5) which shows a higher concentration of waste materials than (4) and is returned into the internal water circulations described above, and the vapours (6) which are introduced in the condensed form into (2); a first concentrate (7), which is added to the bottom exit stream (5), and a first permeate (8), which is fed into (3), flow out of (2); a second concentrate (9), which is recycled into the first reverse osmosis stage (2), and a second permeate (10), which can then be introduced into the biological effluent treatment with considerably improved results, flow out of (3).

Figure 2:
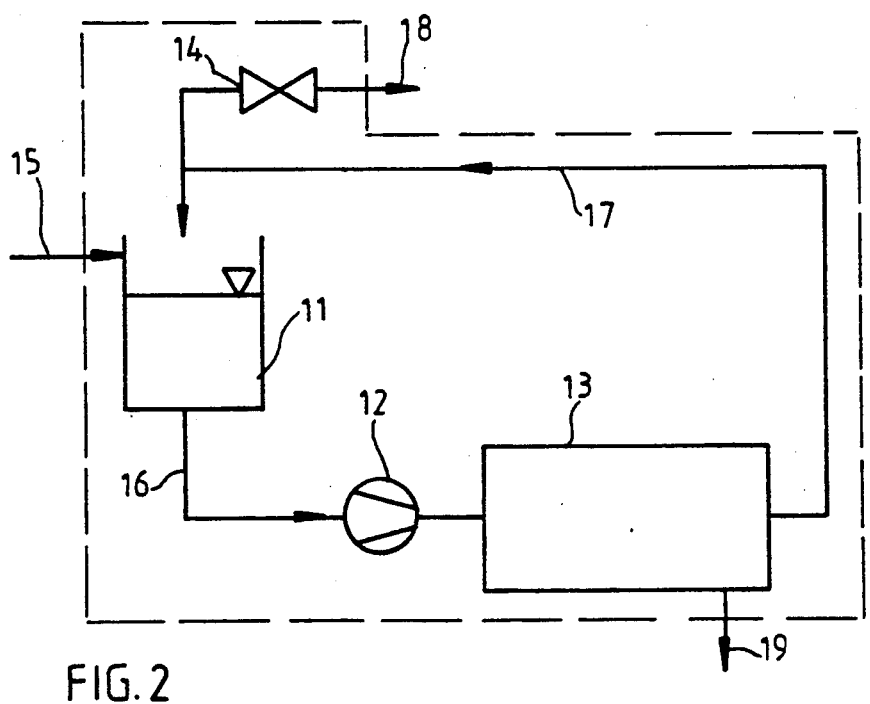
FIG. 2 illustrates details of apparatuses and piping around a membrane module and is useful to explain the setting of the concentration factor CF.

It has also proved to be advantageous, in the case of multi-stage reverse osmosis (preferably in two-stage reverse bsmosis) to operate the various stages (preferably the two stages), under somewhat different process conditions optimised for each stage. The most important optimisation relates to the concentration factor CF, which represents the ratio of the effluent rate being fed to the concentrate taken off and the concentrate still present in the system. The setting of CF may be explained by reference to FIG. 2. The equipment items in FIG. 2 are an effluent feed tank (11), a circulation pump (12), a membrane module (13) and a control valve (14). As material streams, FIG. 2 contains the effluent being fed in (15), the effluent (16) flowing from (11) via (12) to (13), the concentrate stream (17) circulating internally in the reverse osmosis stage, the concentrate (18) taken off via (14) from the reverse osmosis stage and the permeate (19) taken off from the reverse osmosis stage. The equipment items and material streams located in FIG. 2 within the broken line correspond to one of the reverse osmosis stages (2) and/or (3) from FIG. 1. The effluent feed (15) in FIG. 2 corresponds to the feed (6) and/or (8) in FIG. 1. The concentrate (18) taken off in FIG. 2 corresponds to (7) and/or (9) in FIG. 1. Finally, the permeate (19) taken off corresponds to the permeate (8) and/or (10) in FIG. 1.

Under steady conditions, CF is the ratio of the rate (15) to the rate of (18). In the case of the stages nearer the start in the direction of flow, preferably in the first stage, CF is adjusted to from 2 to 16, preferably 6 to 12. In the stages further along, preferably in the second stage in the case of two stages, CF is adjusted to a value from 2 to 14, preferably 3 to 8. For the process according to the invention, the effluent to be purified is adjusted to a pH value from 4 to 9, preferably from 5 to 8. This pH value adjustment is carried out with acids or bases in a manner known in principle to those skilled in the art. For example, $CO_2$, acetic acid and/or sodium hydroxide solution are used for this purpose.

The temperature for the process according to the invention is in the range from 10° to 50° C., preferably 20° to 40° C., particularly preferably 25° to 35° C.

The reverse osmosis according to the invention is operated under a differential pressure of 10 to 60 bar between the inflow side of the membrane and the permeate side. In a preferred way, a differential pressure of 20 to 50 bar is applied. It can also be advantageous, in a multi-stage procedure for the process according to the invention, to run the second or further stages at a pressure tending to be lower than the first stage or the stages nearer the start. In this connection, a differential pressure of 10 to 50 bar, preferably 25 to 35 bar, may be mentioned.

The value of CF which tends to be higher in the first stage or in the first stages in the case of a two-stage or multi-stage procedure gives less concentrate but at a higher concentration, such as can be recycled into the internal water circulations or fed to the waste incineration, and a less well purified permeate. In the last stage or in the last stages in the multi-stage procedure, CF is adjusted to a value which tends to be lower, a more highly purified permeate being achieved and a greater quantity of concentrate, as compared with that at high CF values, being recycled into the first stage or one of the preceding stages. It can therefore be useful to increase the membrane area from stage to stage, for example by 5 to 10% of the area of the preceding stage in each case.

EXAMPLES

General Description

Figure 3:
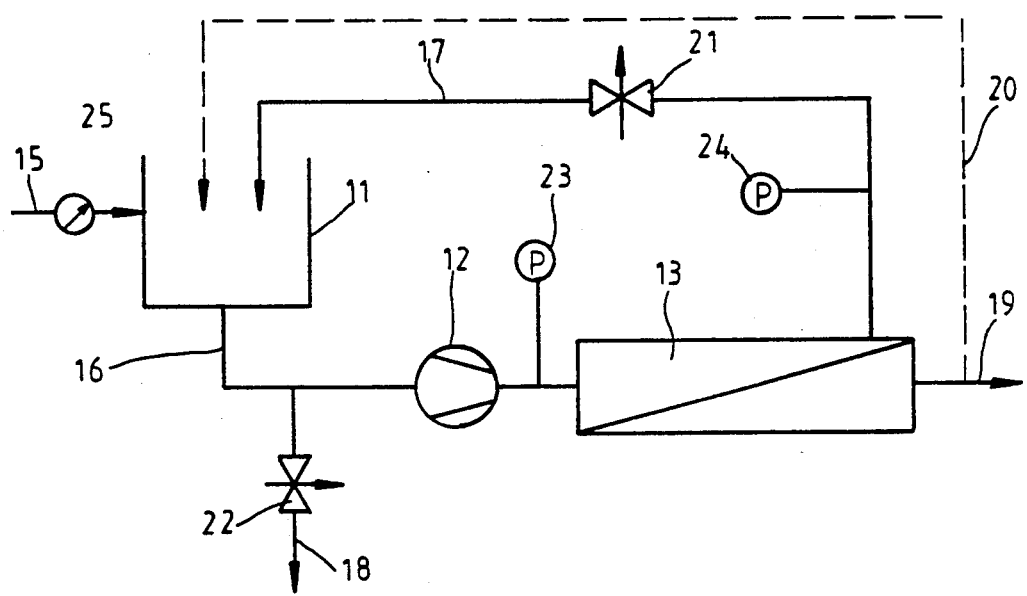
FIG. 3 is in partial agreement with FIG. 2 and shows the apparatus where the working examples of this application were carried out.

The examples were carried out in the apparatus according to FIG. 3. In the latter, in partial agreement with FIG. 2, (11) designates an effluent feed tank, (12) designates a circulation pump, (13) designates a membrane module, (21) and (22) designate two control valves, (23) and (24) designate two pressure-measuring points and (25) designates a water meter. The material streams are the effluent (15) being fed, the effluent (16) fed to the module (13) and including the internal material circulations, the internally circulating concentrate stream (17), the concentrate (18) taken off, the permeate (19) taken off, and the permeate stream (20) which likewise circulates until a stable ratio has been established at the membrane. The total concentrate volume including the feed tank (11) was 230 l, and the permeate volume was 70 l. The batch experiments (limited quantity of effluent) of Examples 1-5 were carried out as follows:

1. filling of the apparatus with effluent via the water meter (about 230 l);

2. start of the reverse osmosis under the conditions indicated for each case, permeate also being recycled into the feed tank (11) during the first hour, in order to establish stable conditions at the membrane (CF=1.3);

3. after this, discharging the permeate and feeding further effluent until 760 l of effluent in total have run in via the water meter (rising CF values), then shutting off the water meter;

4. a further 154 l of permeate were taken off after the effluent had been shut off (CF=10).

In the batch experiment in Example 6, 255 l of a permeate from Example 7 were used as the effluent and thickened up to 44 l of concentrate, with 211 l of permeate taken off (CF=5.8).

In the continuous experimental run according to Example 7 (unlimited effluent quantity), the concentrating was initially taken up to CF=10, that is to say no concentrate was taken off until 2300 l of effluent had been put through and 2070 l of permeate had been produced. After this, 10 l of concentrate were taken off per 100 l of effluent fed.

EXAMPLE 1

Feed: ACN effluent, adjusted with acetic acid to pH 7

WFC membrane (4 m$^2$), v=2.5 m/second, $\Delta P$=40 bar, T=25° C.

| CF | | TOC mg/l | MRC % | COD mg/l | MRC % | NH$_4^{\oplus}$ mg/l | MRC % | Total nitrogen mg/l | MRC % | Flux l/m$^2$h |
|---|---|---|---|---|---|---|---|---|---|---|
| 1 | Feed | 2760 | — | 3270 | — | 325 | — | 1070 | — | — |
|  | Permeate | 510 |  | 620 |  | 11 |  | 225.5 |  |  |
| 1.3 |  |  | 84.4 |  | 84.8 |  | 96.5 |  | 84.1 | 52 |
|  | Concentrate | 3270 |  | 4070 |  | 405 |  | 1420 |  |  |
|  | Permeate | 740 |  | 740 |  | 21 |  | 322.5 |  |  |
| 2.0 |  |  | 84.4 |  | 87.5 |  | 96.9 |  | 84.0 | 47 |
|  | Concentrate | 4750 |  | 5940 |  | 640 |  | 2020 |  |  |
|  | Permeate | 1180 |  | 1130 |  | 33 |  | 655 |  |  |
| 3.3 |  |  | 84.3 |  | 87.7 |  | 96.7 |  | 79.7 | 43 |
|  | Concentrate | 7060 |  | 9205 |  | 990 |  | 3220 |  |  |
|  | Permeate | 1330 |  | 1175 |  | 41 |  | 536 |  |  |
| 5.0 |  |  | 85.9 |  | 90.3 |  | 97.0 |  | 84.2 | 41 |
|  | Concentrate | 9420 |  | 12150 |  | 1370 |  | 3385 |  |  |
|  | Permeate | 1860 |  | 1790 |  | 34 |  | 1130 |  |  |
| 10.0 |  |  | 87.3 |  | 89.3 |  | 98.5 |  | 81.7 | 36 |
|  | Concentrate | 14690 |  | 16600 |  | 2230 |  | 6190 |  |  |

$MRC = \text{Membrane Retention Capacity} = \dfrac{C_{concentrate} - C_{permeate}}{C_{concentrate}}$ TOC = Total Organic Carbon
COD = Chemical Oxygen Demand

EXAMPLE 2

Feed: ACN effluent, adjusted to pH 7 with acetic acid

WFC membrane (4 m$^2$), v=2.5 m/second, $\Delta P$=40 bar, T=35° C.

EXAMPLE 3

Feed: ACN effluent, adjusted with acetic acid to pH 7

WFC membrane (4 m$^2$), v=2.5 m/second, $\Delta P$=35 bar, T=35° C.

| CF | | TOC mg/l | MRC % | COD mg/l | MRC % | NH$_4^{\oplus}$ mg/l | MRC % | Total nitrogen mg/l | MRC % | Flux l/m$^2$h |
|---|---|---|---|---|---|---|---|---|---|---|
| 1 | Feed | 2890 | — | 2975 | — | 320 | — | 1115 | — | — |
|  | Permeate | 530 |  | 521 |  | 10 |  | 227.4 |  |  |
| 1.3 |  |  | 82.7 |  | 86.3 |  | 96.8 |  | 84.6 | 43 |
|  | Concentrate | 3060 |  | 3790 |  | 380 |  | 1480 |  |  |
|  | Permeate | 710 |  | 700 |  | 45 |  | 359.5 |  |  |
| 2.0 |  |  | 84.0 |  | 85.5 |  | 91.5 |  | 83.0 | 45 |
|  | Concentrate | 4450 |  | 4835 |  | 530 |  | 2090 |  |  |
|  | Permeate | 870 |  | 930 |  | 69 |  | 446.5 |  |  |
| 3.3 |  |  | 86.7 |  | 88.9 |  | 93.3 |  | 83.9 | 35 |
|  | Concentrate | 6530 |  | 8400 |  | 970 |  | 2770 |  |  |
|  | Permeate | 1000 |  | 1040 |  | 17 |  | 464 |  |  |
| 5.0 |  |  | 88.4 |  | 88.4 |  | 98.7 |  | 83.3 | 33 |
|  | Concentrate | 8640 |  | 9000 |  | 1260 |  | 2780 |  |  |
|  | Permeate | 1550 |  | 2325 |  | 32 |  | 706 |  |  |
| 10.0 |  |  | 87.9 |  | 86.0 |  | 98.8 |  | 76.9 | 30 |
|  | Concentrate | 12800 |  | 16600 |  | 2650 |  | 3062 |  |  |

| CF | | TOC mg/l | MRC % | COD mg/l | MRC % | NH$_4^{\oplus}$ mg/l | MRC % | Total nitrogen mg/l | MRC % | Flux l/m$^2$h |
|---|---|---|---|---|---|---|---|---|---|---|
| 1 | Feed | 2570 | — | 3620 | — | 275 | — | 1230 | — | — |
|  | Permeate | 630 |  | 653 |  | 50 |  | 296.5 |  |  |
| 1.3 |  |  | 80.0 |  | 82.4 |  | 84.3 |  | 74.7 | 47 |
|  | Concentrate | 3150 |  | 3710 |  | 318 |  | 1170 |  |  |
|  | Permeate | 990 |  | 1050 |  | 22 |  | 450.5 |  |  |
| 2.0 |  |  | 78.1 |  | 82.2 |  | 95.7 |  | 73.6 | 53 |
|  | Concentrate | 4530 |  | 5890 |  | 510 |  | 1705 |  |  |
|  | Permeate | 1300 |  | 1310 |  | 27 |  | 465.5 |  |  |
| 3.4 |  |  | 74.9 |  | 84.5 |  | 96.6 |  | 82.7 | 46 |
|  | Concentrate | 5630 |  | 8470 |  | 790 |  | 2695 |  |  |
|  | Permeate | 1490 |  | 1510 |  | 40 |  | 778 |  |  |
| 5.0 |  |  | 80.0 |  | 86.3 |  | 96.4 |  | 74.4 | 42 |
|  | Concentrate | 7520 |  | 11050 |  | 1100 |  | 3610 |  |  |
|  | Permeate | 440 |  | 1840 |  | 12 |  | 777.5 |  |  |
| 10.0 |  |  | 96.1 |  | 92.3 |  | 99.4 |  | 86.5 | 33 |
|  | Concentrate | 11400 |  | 24000 |  | 2030 |  | 5760 |  |  |

EXAMPLE 4

WFC membrane (4 m²), v=3 m/second, ΔP×40 bar, T=35° C.

| CF | | TOC mg/l | MRC % | COD mg/l | MRC % | $NH_4^{\oplus}$ mg/l | MRC % | Total nitrogen mg/l | MRC % | Flux l/m²h |
|---|---|---|---|---|---|---|---|---|---|---|
| 1 | Feed | 2300 | — | 3635 | — | 295 | — | 1025 | — | — |
|   | Permeate | 510 | | 618 | | 10 | | 173.5 | | |
| 1.3 | | | 81.4 | | 86.3 | | 97.0 | | 86.4 | 58 |
|   | Concentrate | 2740 | | 4495 | | 330 | | 1275 | | |
|   | Permeate | 760 | | 930 | | * | * | 545 | | |
| 2.0 | | | 81.2 | | 86.3 | | | | 70.6 | 60 |
|   | Concentrate | 4040 | | 6805 | | | | 1855 | | |
|   | Permeate | 1110 | | 1255 | | 27 | | 484.5 | | |
| 3.4 | | | 79.4 | | 87.0 | | 96.9 | | 82.7 | 54 |
|   | Concentrate | 5380 | | 10550 | | 870 | | 2795 | | |
|   | Permeate | 1270 | | 1370 | | 25 | | 554.5 | | |
| 5.0 | | | 81.3 | | 88.1 | | 97.7 | | 84.2 | 51 |
|   | Concentrate | 6800 | | 11550 | | 1100 | | 3500 | | |
|   | Permeate | 1920 | | 1930 | | 46 | | 835 | | |
| 10.0 | | | 82.2 | | 91.0 | | 97.5 | | 85.0 | 42 |
|   | Concentrate | 10800 | | 21400 | | 1810 | | 5575 | | |

*was not determined

Feed: ACN effluent, adjusted with acetic acid to pH 7
WFC membrane (4 m²), v=2 m/second, ΔP=40bar, T=35° C.

| CF | | TOC mg/l | MRC % | COD mg/l | MRC % | $NH_4^{\oplus}$ mg/l | MRC % | Total nitrogen mg/l | MRC % | Flux l/m²h |
|---|---|---|---|---|---|---|---|---|---|---|
| 1 | Feed | 2300 | — | 3635 | — | 295 | — | 1025 | — | — |
|   | Permeate | 520 | | 625 | | 5 | | 96 | | |
| 1.3 | | | 80.7 | | 83.9 | | 98.2 | | 92.1 | 51 |
|   | Concentrate | 2700 | | 3890 | | 339 | | 1210 | | |
|   | Permeate | 650 | | 830 | | 10 | | 148 | | |
| 2.0 | | | 81.4 | | 85.6 | | 97.6 | | 91.6 | 55 |
|   | Concentrate | 3500 | | 5760 | | 420 | | 1760 | | |
|   | Permeate | 1000 | | 1320 | | 14 | | 305 | | |
| 3.3 | | | 80.6 | | 84.3 | | 97.8 | | 88.2 | 50 |
|   | Concentrate | 5150 | | 8390 | | 650 | | 2575 | | |
|   | Permeate | 1100 | | 1260 | | 22 | | 348.5 | | |
| 5.0 | | | 83.6 | | 88.7 | | 97.4 | | 88.3 | 43 |
|   | Concentrate | 6700 | | 11150 | | 850 | | 2915 | | |
|   | Permeate | 1770 | | 1795 | | 33 | | 608 | | |
| 10.0 | | | 84.0 | | 90.2 | | 98.2 | | 84.0 | 38 |
|   | Concentrate | 10650 | | 18300 | | 1800 | | 3805 | | |

EXAMPLE 5

Feed: ACN effluent, adjusted with acetic acid to pH 7

| CF | | TOC mg/l | MRC % | COD mg/l | MRC % | $NH_4^{\oplus}$ mg/l | MRC % | Total nitrogen mg/l | MRC % | Flux l/m²h |
|---|---|---|---|---|---|---|---|---|---|---|
| 1 | Feed | 1480 | — | 1765 | — | 41 | — | 590 | — | — |
|   | Permeate | 280 | | 520 | | 7 | | 105 | | |
| 2.0 | | | 88.7 | | 82.2 | | 95.0 | | 90.2 | 17.5 |
|   | Concentrate | 2480 | | 2920 | | 95 | | 1075 | | |
|   | Permeate | 570 | | 760 | | 8 | | 168 | | |
| 4.0 | | | 88.3 | | 88.0 | | 95.3 | | 92.1 | 13.6 |
|   | Concentrate | 4880 | | 6355 | | 170 | | 2125 | | |
|   | Permeate | 680 | | 998 | | 10 | | 248 | | |
| 5.8 | | | 90.4 | | 88.9 | | 94.7 | | 91.3 | 11.8 |
|   | Concentrate | 7080 | | 8975 | | 190 | | 2840 | | |

EXAMPLE 6

Feed: Permeate from Example 7
WFT membrane, T=25° C., ΔP=30 bar

EXAMPLE 7

Feed: ACN effluent, adjusted with acetic acid to pH 7; WFC membrane (4 m²), T=35° C., ΔP=40 bar, v=2.5 m/second ; operating time t in days (d):

| t(d) | CF | | TOC mg/l | MRC % | COD mg/l | MRC % | $NH_4^{\oplus}$ mg/l | MRC % | Total nitrogen mg/l | MRC % | Flux l/m²h |
|---|---|---|---|---|---|---|---|---|---|---|---|
| 1 | 10 | Permeate | 1740 | | 2260 | | 37 | | 720 | | |
|   |   |  | | 84.2 | | 84.4 | | 97.6 | | 85.8 | 25 |
|   |   | Concentrate | 11000 | | 14450 | | 1550 | | 5070 | | |
|   |   | Permeate | 1420 | | 1900 | | 41 | | 602 | | |

-continued

| t(d) | CF | | TOC mg/l | MRC % | COD mg/l | MRC % | NH$_4^\oplus$ mg/l | MRC % | Total nitrogen mg/l | MRC % | Flux l/m²h |
|---|---|---|---|---|---|---|---|---|---|---|---|
| 2 | 10 | | | 88.1 | | 90.3 | | 97.8 | | 89.1 | 23 |
| | | Concentrate | 11900 | | 19600 | | 1850 | | 5525 | | |
| | | Permeate | 1610 | | 2040 | | 49 | | 657 | | |
| 3 | 10 | | | 87.1 | | 90.8 | | 97.4 | | 88.5 | 20 |
| | | Concentrate | 12500 | | 22150 | | 1900 | | 5700 | | |
| | | Permeate | 1510 | | 1860 | | 47 | | 608 | | |
| 4 | 10 | | | 89.0 | | 90.0 | | 97.8 | | 89.4 | 17 |
| | | Concentrate | 13680 | | 18650 | | 2168 | | 5725 | | |
| | | Permeate | 1470 | | 1530 | | 50 | | 612 | | |
| 5 | 10 | | | 88.9 | | 91.1 | | 97.7 | | 89.6 | 13 |
| | | Concentrate | 13200 | | 18350 | | 2165 | | 5890 | | |
| | | Permeate | 1640 | | 1985 | | 65 | | 630 | | |
| 6 | 10 | | | 86.6 | | 90.3 | | 96.2 | | 89.6 | 10 |
| | | Concentrate | 12200 | | 20500 | | 1700 | | 6050 | | |
| | | Permeate | 1620 | | 2050 | | 62 | | 655 | | |
| 7 | 10 | | | 86.4 | | 90.3 | | 96.4 | | 89.2 | 7 |
| | | Concentrate | 11950 | | 21050 | | 1700 | | 6060 | | |

What is claimed is:

1. A process for purifying the effluent arising in the production of acrylonitrile, wherein the effluent is adjusted to a pH value from 4 to 9 and is the subjected to reverse osmosis at a membrane at a temperature from 10° to 50° C. and a differential pressure of 10 to 80 bar, a flow velocity at the membrane being adjusted from 0.5 to 4 m/second.

2. The process of claim 1, wherein the effluent is adjusted to a pH value from 5 to 8.

3. The process of claim 1, wherein the reverse osmosis is carried out at a temperature from 20° to 40° C.

4. The process of claim 1, wherein the differential pressure is from 15 to 60 bar.

5. The process of claim 1, wherein the flow velocity at the membrane is adjusted to from 1 to 3 m/second.

6. The process of claim 5, wherein the flow velocity at the membrane is adjusted to from 1.5 to 2.5 m/second.

7. The process of claim 1, wherein the membrane is used in the form of a flat membrane module, a tubular module or a spirally wound module.

8. The process of claim 7, wherein the membrane is used in the form of a tubular module or a spirally wound module.

9. The process of claim 1, wherein the reverse osmosis is carried out in a plurality of stages.

10. The process of claim 9, wherein the reverse osmosis is carried out in two stages.

11. The process of claim 9, wherein the stages which are nearer the start in the direction of flow are fitted with a tubular module and the stages further along are fitted with a spirally wound module.

12. The process of claim 11, wherein the first stage is fitted with a tubular module.

13. The process of claim 10, wherein the first stage is fitted with a tubular module and the second stage is fitted with a spirally wound module.

14. The process of claim 9, wherein concentration factor CF as a ratio of the effluent rate being fed to the concentrate taken off and the concentrate still present in the system is adjusted to CF=2 to 16 in the case of the stages nearer the start in the direction of flow and adjusted to CF=2 to 14 in the stages further along.

15. The process of claim 14, wherein the concentration factor CF is adjusted to CF=6 to 12 in the case of the stages nearer the start in the direction of flow.

16. The process of claim 14, wherein the concentration factor CF is adjusted to CF=3 to 8 in the stages further along.

17. The process of claim 14, wherein in the case of two stages the concentration factor CF is adjusted to CF=6 to 12 in the first stage and to CF=3 to 8 in the second stage.

* * * * *